United States Patent [19]

Peng

[11] Patent Number: 5,101,843
[45] Date of Patent: Apr. 7, 1992

[54] DENTAL FLOSS WITH HOLDER USED IN FIXED ORTHODONTIC APPLIANCE

[76] Inventor: Chien-Lun Peng, 7F., 4, Alley 7, Lane 53, Sec. 4, Nanking E. Rd., Taipei, Taiwan

[21] Appl. No.: 640,899

[22] Filed: Jan. 14, 1991

[51] Int. Cl.⁵ .......................................... A61C 15/00
[52] U.S. Cl. ................................................ 132/323
[58] Field of Search .............. 132/323, 324, 325, 326, 132/327, 329

[56] References Cited

U.S. PATENT DOCUMENTS

| D. 251,074 | 2/1979 | Schiff | 132/323 X |
|---|---|---|---|
| 806,300 | 12/1905 | Sorenson | 132/323 X |
| 1,213,667 | 1/1917 | McKinney | 132/325 |
| 3,918,466 | 11/1975 | Peebles, Jr. | 132/323 |
| 4,013,085 | 3/1977 | Wright | 132/323 |
| 4,192,330 | 3/1980 | Johnson | 132/323 |
| 4,727,895 | 3/1988 | Berarducci | 132/323 |
| 5,014,725 | 5/1991 | Patscot et al. | 132/323 X |

FOREIGN PATENT DOCUMENTS 2842404 4/1980 Fed. Rep. of Germany ...... 132/323

Primary Examiner—Robert P. Swiatek
Assistant Examiner—Nicholas D. Lucchesi
Attorney, Agent, or Firm—Asian Pacific International Patent and Trademark Office

[57] ABSTRACT

A dental flosser suitable to be used with a fixed orthodontic appliance, provided for a wearer to clean food debris and dental plaque so as to prevent an orthodontic appliance wearer from getting proximal caries and periodontal disease during orthodontic treatment period, the dental flosser including a hold portion, a floss portion and two floss supports wherein the floss supports are outwardly curved and more slender than prior art devices and the hold portion can be held on both sides so that the floss supports can be inserted into the narrow clearance between the orthodontic wire and teeth, allowing the connected floss to intrude into the adjacent surfaces of the teeth and by means of the outwardly curved floss supports, the operating space in the narrow clearance is enlarged so that the floss can fully scrape off the food debris and dental plaque on the teeth.

4 Claims, 2 Drawing Sheets

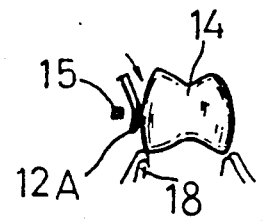
FIG.5-A
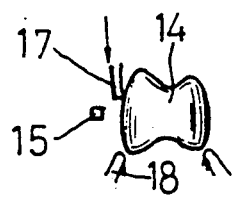
FIG.5-B PRIOR ART
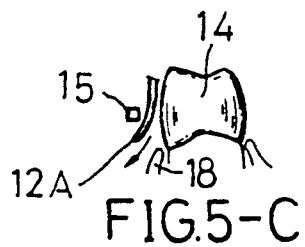
FIG.5-C
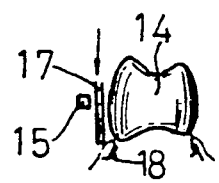
FIG.5-D PRIOR ART
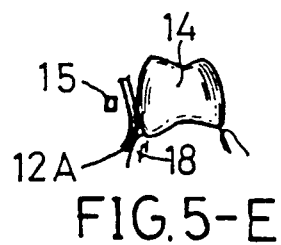
FIG.5-E
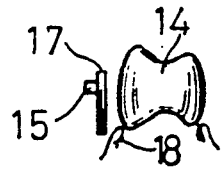
FIG.5-F PRIOR ART
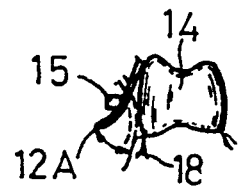
FIG.5-G
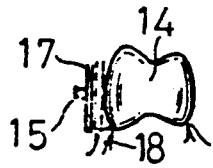
FIG.5-H PRIOR ART

DENTAL FLOSS WITH HOLDER USED IN FIXED ORTHODONTIC APPLIANCE

BACKGROUND OF THE INVENTION

The present invention relates to a dental flosser used in fixed orthodontic appliances. The dental flosser includes a strand of dental floss, two floss supports and a holder portion. The floss supports and holder portion are specially designed to be suitably used in fixed orthodontic appliance.

A dental flosser is used in such a manner that the dental floss is intruded between the adjacent surfaces of two teeth and into the gingival sulcus and then the floss is urged to scrape the surfaces to clean up the food debris and dental plaque. The dental flosser appears to be a most effective tool for cleaning the adjacent surfaces of the teeth in cooperation with the toothbrush. However, during orthodontic treatment period, a fixed orthodontic appliance will be applied to a patient and a metal orthodontic wire will be fixed between the teeth so that the conventional flosser is unable to go between the teeth so as to perform up and down left and right scraping movements. In addition, the conventional dental flosser is not designed in accordance with the requirement of a patient under orthodontic procedure. The excessively thick floss supports can not go through the quite narrow clearance between the metal orthodontic wire and the adjacent surface of the teeth. (The clearance between the metal orthodontic wire and the adjacent surface of the teeth is referred hereinafter as "clearance".) Therefore, the complications of proximal caries and periodontal disease often occur in orthodontic procedure to bother the patients and the doctors.

SUMMARY OF THE INVENTION

It is a primary object of this invention to provide a dental flosser with specifically designed floss supports and holder portion to be suitably used in a fixed orthodontic appliance so that the patient can clean the adjacent surfaces of the teeth himself/herself to prevent dental complications.

Accordingly, the present invention is characterized by the following features:

1. more slender floss supports (with diameter less than 1 mm), capable of sufficiently moving in the clearance;

2. curved floss supports suitable to conveniently rotarily go into the clearance and operate within the clearance with enlarged moving range;

3. symmetric hold portion which can be held on both sides so that the dental floss can be utilized throughout its length; and 4. the inner sides of the holder portion adjacent to the floss supports are relatively slender and the outer sides of the hold portion are widened to prevent the floss support from breaking due to its fineness. The holder portion is widened in accordance with the distance between the incisal edge and cusp tip of the teeth and the metal orthodontic wire so that the floss supports can be strengthened without affecting normal operation.

BRIEF DESCRIPTION OF THE DRAWINGS

FIG. 5A-5H are views comparing the curved floss supports of this invention with conventional straight floss supports.

DETAILED DESCRIPTION OF THE PREFERRED EMBODIMENTS

Figure 1:
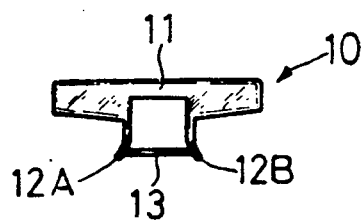
FIG. 1 is a front view of this invention.
Figure 2:
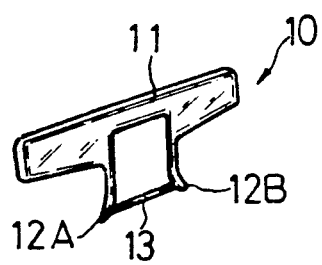
FIG. 2 is a perspective view thereof.

Please first refer to FIGS. 1 and 2. The dental flosser 10 of this invention includes a flat holder panel 11 having a relatively narrow central portion and two relatively wide wing portions. Two slender prong-like floss supports 12A and 12B extend from panel 11 at the junctures between the central panel portion and the wing portions. The wing portions are wider than the middle part thereof for enhancing the support effect of the floss supports 12A, 12B and for the convenience of use. A strand of dental floss 13 is disposed between the floss supports 12A, 12B at the free ends thereof.

Figure 3:
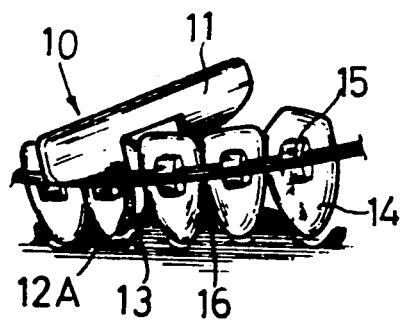
FIG. 3 is a perspective view, showing the application of this invention to the teeth.

Referring to FIG. 3, the curved floss supports 12A, 12B are placed into the clearance between the teeth 14 and a metal orthodontic wire 15, permitting the floss 13 to clean up the adjacent surfaces 16 of the teeth 14.

Figure 4:
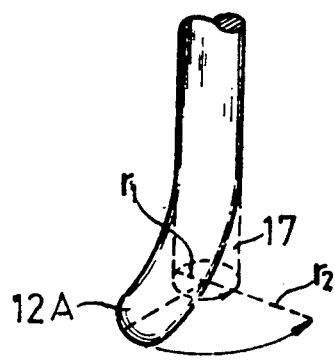
FIG. 4 shows the curved design of the floss support.

Please now refer to FIG. 4, which shows an enlarged view of the curved floss support 12A, wherein the curved floss support 12A is denoted by solid line while a straight floss support 17 is denoted by dotted line. The arrows respectively show a large arc moving range of the curved floss support 12A and a small arc moving range of the straight floss support 17. Since the radius r1 of the moving range of the straight floss support is smaller than the radius r2 of the moving range of the curved floss support, therefore the operation range of the curved floss supports 12A, 12B between the teeth 14 and metal orthodontic wire is extended so that the dental floss can fully scrape the adjacent surfaces of the teeth up and down and left and right.

Please refer to FIGS. 5A, 5B, in which the curved floss support 12A is compard with the straight floss support 17, wherein the sectional views of the tooth 14, gums 18 and metal orthodontic wire 15 are shown. When the curved floss supports 12A goes into the clearance between the tooth 14 and the metal orthodontic wire 15, the curved floss support 12A first abuts against the adjacent surface of the tooth 14 and then rotarily goes into the clearance. While the straight floss support 17 must be first aligned with the clearance and then inserted thereinto. Therefore, the using manner of the straight floss support 17 is not so easy as that of the curved floss support 12A. Such manner of rotarily entering the clearance is an advantage of the operation of curved floss supports 12A, 12B. As shown in FIGS. 5C, 5D, after the curved floss support 12A enters the clearance, it will gradually leave the gums 18 while the straight floss support 17 is straightly inserted and apt to injure the gums 18.

Please now refer to FIGS. 5E and 5F, wherein the curved floss support 12A meets the shape of the gums 18 so that a complete and safe cleaning effect can be achieved while the straight floss support is not corresponding to the shape of the gums 18 so that it is easy to injure the gums 18 in operation.

Please now refer to FIGS. 5G and 5H, wherein the maximum operation range of the curved floss support 12A is shown. The curved floss support 12A can closely inward abut against the surface of the gums 18 and outward extend outside the metal orthodontic wire 15.

While the straight floss support 17 is limited within a space between the orthodontic wire and the teeth. The operation range of the curved floss support 12A is obviously larger than that of the straight floss support 17.

Figure 6:
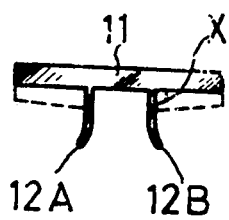
FIG. 6 shows the widened design of the hold portion of this invention.

Please now refer to FIG. 6, wherein the holder portion 11 of the dental floss of this invention is shown. Because the diameter of the curved floss supports 12A, 12B is about 0.5–1.0 mm, therefore if the curved floss supports 12A, 12B are designed too long, they will be apt to distort and break. To shorten the length of the curved floss supports 12A, 12B, the hold portion 11 therebeside is widened so that the curved floss supports 12A, 12B are enhanced to sufficiently support the dental floss 13 without distortion.

In FIG. 6, the dotted line indicates the conventional design of the hold portion while the solid line indicates the widened holder portion 11 of this invention. The widened portion thereof is about 3.5 mm wide, as indicated by "X", corresponding to the distance between the metal orthodontic wire 15 and the occlusal surface.

As indicated, the structure herein may be variously embodied. Recognizing various modifications will be apparent, the scope hereof shall be deemed to be defined by the claims as set forth below.

What is claimed is:

1. A dental flossing device for use by a person having a fixed orthodontic appliance affixed to his or her teeth; said flossing device comprising a flat planar holder panel comprising at least one substantially rectangular section; two relatively slender prongs extending from said holder panel within the panel plane; said prongs having straight parallel sections thereof connected to said panel and curved free distal ends; said distal free ends of said prongs curving away from each other while remaining within the plane of the panel; and a strand of dental floss connected between the curved free ends of the slender prongs; each prong being thin enough to extend through a clearance between an orthodontic wire and the juncture zone between two teeth, such that the strand of dental floss can extend through the teeth juncture zone to engage the gum area.

2. The flossing device of claim 1, wherein each prong has a length such that when the strand of dental floss is engaged with the user's gum the flat panel has an edge thereof in near proximity to an orthondontic wire.

3. The flossing device of claim 1, wherein said panel has a central portion bridging the space between said prongs and two wing portions extending in opposite directions from the central portion; each wing portion of the panel having one edge thereof extending from one of the prongs; said central portion of the panel having a central connector edge thereof connected to both prongs; said one edge of each wing portion being closer to the free end of the associated prong than the connector edge of the panel central portion, whereby said wing portions stiffen the prongs without obstructing the space between the prongs.

4. The flossing device of claim 1, wherein the prongs are spaced apart by a distance slightly greater than the front-to-rear dimension of a person's tooth, whereby when the strand of dental floss is engaged with the person's gums the free ends of both prongs will be in near proximity to the gum area.

* * * * *